(12) United States Patent
Loori et al.

(10) Patent No.: US 8,529,527 B2
(45) Date of Patent: Sep. 10, 2013

(54) CONTROLLER FOR AN EXTREMITY HYPERBARIC DEVICE

(75) Inventors: Phillip Loori, Farmingdale, NJ (US); George Hovorka, East Boston, MA (US)

(73) Assignee: AOTI, Inc., Tamarac, FL (US)

( * ) Notice: Subject to any disclaimer, the term of this patent is extended or adjusted under 35 U.S.C. 154(b) by 1128 days.

(21) Appl. No.: 12/156,466

(22) Filed: May 30, 2008

(65) Prior Publication Data

US 2009/0126727 A1    May 21, 2009

Related U.S. Application Data

(60) Provisional application No. 60/932,708, filed on May 31, 2007, provisional application No. 61/002,077, filed on Nov. 6, 2007.

(51) Int. Cl.
*A61F 13/00* (2006.01)

(52) U.S. Cl.
USPC .......................................... 604/305; 604/540

(58) Field of Classification Search
USPC ............ 604/540, 23–26, 290–293, 317–321, 604/333, 337, 543, 305, 289; 600/21; 128/202.12; 601/11, 27, 33, 43, 48, 165–166; 428/718; 137/542
See application file for complete search history.

(56) References Cited

U.S. PATENT DOCUMENTS

| | | | |
|---|---|---|---|
| 871,760 A | 11/1907 | Long et al. | |
| 1,117,168 A | 11/1914 | Crowley | |
| 2,134,646 A | 10/1938 | Sauzedde | |
| 3,368,556 A | 2/1968 | Jensen et al. | |
| 3,478,738 A | 11/1969 | Altman et al. | |
| 3,602,221 A | 8/1971 | Bleiken | |
| 3,604,421 A | 9/1971 | Pizzella | |
| 3,669,096 A | 6/1972 | Hurwitz | |
| 3,701,349 A | 10/1972 | Larson | |

(Continued)

FOREIGN PATENT DOCUMENTS

| DE | 19846922 A1 | 4/2000 |
|---|---|---|
| EP | 0392669 A2 | 10/1990 |

(Continued)

OTHER PUBLICATIONS

International Search Report, PCT/US08/06883.

(Continued)

*Primary Examiner* — Tatyana Zalukaeva
*Assistant Examiner* — Benedict L Hanrahan
(74) *Attorney, Agent, or Firm* — Lerner, David, Littenberg, Krumholz & Mentlik, LLP

(57) ABSTRACT

A controller is operable to selectively supply gas to, and evacuate gas from, regions of a hyperbaric wound treatment chamber. The controller operates to inflate a passage or rib of the device to provide that the device is made sufficiently rigid for inserting a limb therethrough, and inflate an inflatable cuff to create a seal against the limb. The controller also operates to evacuate ambient air trapped within the chamber, and optionally partially evacuate the passage or rib, after the seal is created by the inflatable cuff, and then introduce oxygen into the chamber, and optionally inflate the passage or rib. The cuff, when inflated and creating a seal against a limb, optionally is at least partially within the chamber, and the treatment gas is supplied to the chamber to maintain the seal of the cuff against the limb.

28 Claims, 8 Drawing Sheets

(56) References Cited

U.S. PATENT DOCUMENTS

| | | | |
|---|---|---|---|
| 3,712,298 A | 1/1973 | Snowdon et al. | |
| 3,744,491 A | 7/1973 | Fischer | |
| 3,785,374 A | 1/1974 | Lipson | |
| 3,920,006 A | 11/1975 | Lapidus | |
| 3,955,565 A | 5/1976 | Johnson, Jr. | |
| 4,003,371 A | 1/1977 | Fischer | |
| 4,211,223 A | 7/1980 | LoPiano | |
| 4,227,524 A | 10/1980 | Galerne | |
| 4,236,513 A | 12/1980 | LoPiano | |
| 4,280,489 A | 7/1981 | Johnson, Jr. | |
| 4,328,799 A | 5/1982 | LoPiano | |
| 4,331,133 A | 5/1982 | Arkans | |
| 4,346,699 A | 8/1982 | Little et al. | |
| 4,353,359 A | 10/1982 | Milbauer | |
| 4,363,317 A | 12/1982 | Broucek | |
| 4,378,009 A | 3/1983 | Rowley et al. | |
| 4,460,370 A | 7/1984 | Allison et al. | |
| 4,628,945 A | 12/1986 | Johnson, Jr. | |
| 4,633,859 A | 1/1987 | Reneau | |
| 4,635,635 A | 1/1987 | Robinette-Lehman | |
| 4,667,672 A | 5/1987 | Romanowski | |
| 4,801,291 A | 1/1989 | Loori | |
| 5,007,411 A | 4/1991 | Dye | |
| 5,029,579 A | 7/1991 | Trammell | |
| 5,060,644 A | 10/1991 | Loori | |
| 5,125,400 A | 6/1992 | Johnson, Jr. | |
| 5,154,697 A | 10/1992 | Loori | |
| 5,211,642 A | 5/1993 | Clendenning | |
| 5,234,459 A | 8/1993 | Lee | |
| 5,264,218 A | 11/1993 | Rogozinski | |
| 5,312,385 A | 5/1994 | Greco | |
| 5,376,067 A | 12/1994 | Daneshvar | |
| 5,413,582 A * | 5/1995 | Eaton | 606/202 |
| 5,437,602 A | 8/1995 | Polyakov et al. | |
| 5,458,562 A | 10/1995 | Cooper | |
| 5,478,310 A | 12/1995 | Dyson-Cantwell et al. | |
| 5,578,055 A | 11/1996 | McEwen | |
| 5,605,534 A | 2/1997 | Hutchison | |
| 5,620,001 A | 4/1997 | Byrd et al. | |
| 5,660,182 A | 8/1997 | Kuroshaki et al. | |
| 5,669,390 A | 9/1997 | McCormick et al. | |
| 5,678,543 A | 10/1997 | Bower | |
| 5,688,236 A | 11/1997 | Gragg | |
| 5,738,093 A | 4/1998 | Santi | |
| 5,810,795 A | 9/1998 | Westwood | |
| 5,865,722 A | 2/1999 | Heng | |
| 6,007,559 A | 12/1999 | Arkans | |
| 6,120,860 A | 9/2000 | Bowen et al. | |
| 6,235,365 B1 | 5/2001 | Schaughency et al. | |
| 6,321,746 B1 | 11/2001 | Schneider et al. | |
| 6,622,326 B2 | 9/2003 | Richardson | |
| 6,702,794 B2 | 3/2004 | Blum et al. | |
| 6,793,644 B2 | 9/2004 | Stenzler | |
| 6,814,720 B2 | 11/2004 | Olsen et al. | |
| 6,881,929 B2 | 4/2005 | Hovorka | |
| 7,540,283 B2 * | 6/2009 | Loori et al. | 128/202.12 |
| 7,998,125 B2 * | 8/2011 | Weston | 604/317 |
| 2003/0036771 A1 | 2/2003 | McEwen et al. | |
| 2005/0161039 A1 * | 7/2005 | Gurnee et al. | 128/202.12 |
| 2005/0261615 A1 * | 11/2005 | Weston | 602/13 |
| 2006/0185670 A1 * | 8/2006 | Loori et al. | 128/202.12 |
| 2007/0037472 A1 | 2/2007 | Greenwald et al. | |
| 2008/0140029 A1 | 6/2008 | Smith et al. | |
| 2009/0120433 A1 * | 5/2009 | Loori et al. | 128/202.12 |

FOREIGN PATENT DOCUMENTS

| | | |
|---|---|---|
| JP | 45-022313 | 7/1970 |
| JP | 2008531113 A | 8/2008 |
| WO | 2006091243 | 8/2006 |

OTHER PUBLICATIONS

U.S. Appl. No. 61/002,269; filed Nov. 7, 2007, entitled "Pressure Compensating Seal With Positive Feedback".
U.S. Appl. No. 11/064,581; Feb. 24, 2005, entitled "Hyperbaric Oxygen Device and Delivery methods".
U.S. Appl. No. 12/156,465; filed May 30, 2008, entitled "Controller for an Extremity Hyperbaric Chamber".
U.S. Appl. No. 12/291,317.
U.S. Appl. No. 12/291,348.
U.S. Appl. No. 12/291,328.
U.S. Appl. No. 12/291,342.
U.S. Appl. No. 12/291,347.
U.S. Appl. No. 12/291,338.
The Topical Hyperbaric Oxygen Extremity Chamber.
The Disposable Sacral Topical Hyperbaric Oxygen System.
Dutton, et al. "Topical Hyperbaric Oxygen Therapy: A Case Study" Macassa Lodge, Hamilton, Ontario.
Heng, et al. "Angiogenesis in Necrotic Ulcers Treated with Hyperbaric Oxygen" OstomyWound Management, Sep. 2000, vol. 46, Issue 9, pp. 18-32.
Edsberg, et al. "Use of Topical Hperbaric Oxygen for Treatment of Chronic Wounds in Long-Termn Health Care Facilities" Natural & Health Sciences Research Center, Daemen College, Amherst, NY.
Edsberg, et al. "Reducing Epibole Using Topical Hyerpbaric Oxygen and Electrical Stimulation" OstomyWound Management Apr. 2002, vol. 48, Issue 4, pp. 26-29.
Diamond, et al. "The Effect of Hyperbaric Oxygen on Lower Extremity Ulcerations" Journal of the American Podiatry Association, vol. 72, No. 4, Apr. 1982, pp. 180-185.
Lehman, et al. "Human Bite Infections of the Hand: Adjunct Treatment with Hyperbaric Oxygen" Orthopedic Complications, Infections in Surgery, Jun. 1985, pp. 460-465.
Fischer "Topical Hyperbaric Oxygen Treatment of Pressure Sores and Skin Ulcers" reprinted from the Lancet, Aug. 23, 1969, pp. 405-409.
Upson "Topical Hyperbaric Oxygenation in the Treatment of Recalcitrant Open Wounds—A clinical report" Physical Therapy, vol. 66, No. 9, Sep. 1986, pp. 1408-1411.
Fischer "Treatment of Ulcers on the Legs with Hyperbaric Oxygen" reprinted from The Journal of Dermatologic Surgery, Inc. vol. 1, No. 3, Oct. 1975, J of Derm Surg 1:3, Oct. 1975, pp. 55-58.
Heng "Topical Hyperbaric Therapy for Problem Skin Wounds" J Dermatol Surg Oncol. Aug. 1993; 19(8):784-93, Department of Medicine, UCLA San Fernando Valley Internal Medicine Program, Veterans Administration Medical Center, Sepulveda, PMID: 8349920 [PubMed—indexed for MEDLINE].
Kalliainen, et al. "Topical oxygen as an adjunct to wound healing: a clinical case series" ISP Pathophysiology 9 (2003) 81-87, 2002 Elsevier Science Ireland Ltd.
Kaufman, et al., "Topical oxygen and burn wound healing: a review" Shriners Burns Institute, Cincinnati Unit, Ohio.
Olejniczak, et al. "Topical Oxygen Promotes Healing of Leg Ulcers" Dec. 1976, Medical Times, vol. 104, No. 12, pp. 115-120.
Fries, et al., "Dermal excisional wound healing in pigs following treatment with topically applied pure oxygen" Mutat. Res. Nov. 11, 2005; 579(1-2): 172-81 Epub 2005 Aug 18, Laboratory of Molecular Medicine, Dorothy M. Davis Heart and Lung Research Institute and Comprehensive Wound Center, Department of Surgery, The Ohio State University Medical Center, Columbus, OH, PMID: 16105672 [PubMed—in process].
Stryker—Taoti Advanced Oxygen Therapy, Inc. Wound Care Solution Excellence, Strategic Discussions Kalamazoo, Michigan, Mar. 21, 2007 powerpoint presentation, 96 pages.
Venous Ulcers Appendix I, Evidence Table per FDA Draft Guidance Document, 8 pages.
Clinical Device Group and the Food and Drug and Law Institute are happy to present: "Getting CMS Reimbursement for Medical Technology Product" 2006, Clinical Device Group, Inc. Powerpoint presentation, 78 pages.
Medical Coverage Advisory Committee, Usual Care of Chronic Wounds, Powerpoint presentation, 144 pages.
CDC Diabetes, Department of Health and Human Services, Centers for Disease Control and Prevention, "National Diabetes Fact Sheet", United States, 2003, General Information, 3 pages.
Pompeo "The Role of "Wound Burden" in Determining the Costs associated with Wound Care" OstonomyWound Management, Mar. 2001, vol. 47, Issue 3, pp. 65-71.

Frykberg, et al. "Diabetic Foot Disorders: A Clinical Practice Guideline" 2006 revision, The Journal of Foot and Ankle Surgery, vol. 45, No. 5, Sep./Oct. 2006, S1-S66.

American Diabetes Association, "Economic Costs of Diabetes in the U.S. In 2002" Diabetes Care, vol. 26, No. 3, Mar. 2003, pp. 917-932.

Snyder, et al. OstomyWound—Osteomyelitis in the Diabetic Patient: Overview, Diagnosis, Microbiology, "Osteomyelitis in the Diabetic Patient: Diagnosis and Treatment Part 1: Overview, Diagnosis, and Microbiology" (Abstract).

Branom, et al., "'Constant Force Technology' versus Low-Air-Loss Therapy in the Treatment of Pressure Ulcers", OstomyWound—Utilizing a Systems Approach to Implement Pressure Ulcer Prediction and Prevention, Sep. 2001, vol. 47, Issue 9, pp. 38-39.

Landau, et al. "Topical hyperbaric oxygen and low energy laser therapy for chronic diabetic foot ulcers resistant to conventional treatment" Yale J. Biol. Med. Mar.-Apr. 2001; 74(2):95-100, The Hebrew University, Hadassah School of Medicine, Jerusalem, Israel. PMID: 11393266 [PubMed—indexed for Medline].

Sen, et al. "Oxygen, oxidants, and antioxidants in would healing: an emerging paradigm" Laboratory of Molecular Medicine, Dorothy M. Davis Heart and Lung Research Institute, Department of Surgery (CMIS), The Ohio State University Medical Center, Columbus, OH, Ann n. Y. Acad. Sci. May 2002; 957:239-49, PMID: 12074976 [PubMed—indexed for MEDLINE].

Gordillo, et al. "Revisiting the essential role of oxygen in wound healing" Department of Surgery, Laboratory of Molecular Medicine, 512 Davis Heart and Lung Research Institute, The Ohio State University, 473 West 12th Ave., Columbus, OH, Am. J. Surg. Sep. 2003;186(3):259-63, PMID: 12946829 [PubMed—indexed for MEDLINE].

Ignacio, et al. "Topical Oxygen Therapy Treatment of Extensive Leg and Foot Ulcers" Journal of the American Podiatric Medical Association, vol. 75, No. 4, Apr. 1985, pp. 196-199.

Cianci "Advances in the treatment of the diabetic foot: Is there a role for adjunctive hyperbaric oxygen therapy?" Wound Repair Regen, Jan.-Feb. 2004; 129(1):2-10, Department of Hyperbaric Medicine, Doctors Medical Center, San Pablo, California, PMID: 14974958 [PubMed—indexed for MEDLINE].

Hopf, et al. "Hyperoxia and angiogenesis" Blackwell Synergy: Wound Repair Regen, vol. 13, Issue 6, pp. 558-564: Hyperoxia and angiogenesis (Abstract); Wound Repair and Regeneration vol. 13 Issue 6 p. 558—Nov. 2005; http://www.blackwell-synergy.com/doi/abs/10.1111/j.1524-475X.2005.00078.x(1of 3) Dec. 19, 2006.

Kaufman, et al. "The Microclimate Chamber: The Effect of Continuous Topical Administration of 96% Oxygen and 75% Relative Humidity on the Healing Rate of Experimental Deep Burns" The Journal of Trauma, vol. 23, No. 9, pp. 806-815.

Heng, et al. "Endothelial cell toxicity in leg ulcers treated with topical hyperbaric oxygen" Am. J. Dermatopathol Oct. 1986; 8(5):403-10; MID: 3777378 [PubMed—indexed for MEDLINE].

Heng, et al. "Enhanced Healing and Cost-Effectiveness of Low—Pressure Oxygen Therapy in Healing Necrotic Wounds: A feasibility study of technology transfer" Ostomy/Wound Management 2000; 46(3):52-62; From the Division of Dermatology, Department of Medicine, Department of Veterans Affairs, VAGLAHS (Sepulveda), UCLA San Fernando Valley Program, pp. 52-60.

Harkless, et al. "Seven keys to Treating Chronic Wounds" Diabetes Watch, Podiatry Today, Dec. 2000, pp. 17-19.

Diabetes Care, published by the American Diabetes Association "Study Finds Diabetes Will Double in World by 2030: Predicts Rapid U.S. increase That Greatly Exceeds Prior CDC Projections" lead author Dr. Sarah Wild, Public Health Sciences, University of Edinburgh, 2 pages.

Rossi, Hudson Podiatry Center, Letter.

International Search Report, PCT/US2008/12669, dated Dec. 27, 20008.

International Search Report, PCT/US2008/12625, dated Dec. 22, 2008.

International Search Report, PCT/US08/12535, dated Dec. 25, 2008.

* cited by examiner

CONTROLLER FOR AN EXTREMITY HYPERBARIC DEVICE

CROSS REFERENCE TO RELATED APPLICATIONS

This application claims the benefit of the filing dates of U.S. Provisional Patent Application No. 60/932,708 filed May 31, 2007 and U.S. Provisional Patent Application No. 61/002,077 filed Nov. 6, 2007, the disclosures of which are hereby incorporated by reference.

BACKGROUND

Hyperbaric chambers are devices which create sealed environments for the application of therapeutic gases to hasten healing of lesions or wounds on a patient's body. See U.S. Pat. No. 5,060,644, the disclosure of which is incorporated herein by reference. The introduction of pressurized oxygen into such an encapsulated environment promotes healing of various types of lesions and wounds. In particular, the treatment of lesions and wounds with hyperbaric chambers, in conjunction with various stimuli, promotes granulation, raises the capillary blood oxygen pressure and increases expression of angiogenesis related growth function VEGF, HB EGI and KGF, thereby stimulating leukocyte function necessary to suppress bacterial proliferation. The introduction of humidity into hyperbaric chambers can also produce positive results.

When hyperbaric chambers were first introduced for healing lesions and wounds, they encompassed the entire body. As time progressed, hyperbaric chambers became more sophisticated and included multiple functions, and topical hyperbaric chambers also were developed, such as described in U.S. Pat. No. 5,060,644.

There still exists a need, however, for a hyperbaric wound treatment apparatus and method for treating a variety of wounds or lesions on a patient's body with high efficacy and a short treatment time.

SUMMARY OF INVENTION

In accordance with one aspect of the invention, a hyperbaric wound treatment device includes a chamber having an interior and an open end in communication therewith, and an inflatable limb sleeve coupled to the chamber and which can be positioned at least partially within the interior of the chamber adjacent the open end of the chamber.

In one embodiment of the invention, a method of operating a hyperbaric wound treatment device includes inserting a limb through an inflatable limb sleeve and into an open end of a chamber of the device, where the sleeve is coupled to the chamber and can be positioned at least partially within the chamber at the open end. The method further includes inflating the sleeve to an inflated condition when the limb is positioned within the sleeve, thereby sealing the sleeve about the limb.

In another embodiment, a hyperbaric wound treatment device includes a chamber having an open end, and a means coupled to the chamber for receiving a limb of a patient therethrough. The means is inflatable from a first condition whereby the means is capable of receiving the limb to a second condition whereby the means forms at least a partial seal about the limb. When in the second condition, the means can be positioned at least partially within the chamber adjacent the open end of the chamber.

In a further embodiment, a hyperbaric wound treatment device for treatment of a limb of a patient includes a flexible chamber defining an interior adapted to receive a portion of a patient's limb to be treated therein, where the chamber has an open end in communication with the interior of the chamber. The device further includes an inflatable sleeve coupled to the chamber adjacent the open end, and the sleeve includes an outer wall spaced from an inner wall defining an interior region therebetween. At least a portion of the sleeve is extendable into the interior of the chamber adjacent the open end thereof. The sleeve is inflatable between a first condition whereby the patient's limb can be inserted through the sleeve into a portion of the interior of the chamber, and a second condition whereby the sleeve forms at least a partial seal about the patient's limb while received within the chamber.

In another aspect of the invention, a controller for controlling a hyperbaric wound treatment device includes a gas conveyance assembly operable for creating a negative pressure, and a control device which is coupled to the gas conveyance assembly. The control device is operable to control the gas conveyance assembly for providing that a portion of the gas conveyance assembly is in fluid communication with the treatment device; and for creating a negative pressure within the treatment device by evacuating gas, such as ambient air, at least partially from within the treatment device.

In one embodiment, a hyperbaric wound treatment control apparatus includes a means for creating a negative pressure within at least a portion of a hyperbaric wound treatment device. The apparatus further includes a controller coupled to and operable for controlling the means for providing that the means is in fluid communication with the portion of the device; and for creating a negative pressure within the portion of the device by evacuating gas at least partially from within the portion of the device.

In another embodiment, a method of conveying gas to and from a hyperbaric wound treatment device includes creating a negative pressure in a treatment chamber of the device after inserting a limb through an open end of the treatment chamber and sealing the chamber at the open end. The method further includes evacuating gas at least partially from within the treatment chamber, and supplying a treatment gas to the treatment chamber following the evacuation of the gas from the treatment chamber.

In still another embodiment, a method of controlling flow of gas to and from a collapsible hyperbaric wound device includes inflating an inflatable rib of the device, which is for retaining the device in a rigid state, with a gas at least partially, before inserting a limb into a treatment chamber of the device having an open end. The method further includes inflating an inflatable sleeve of the device, which is for receiving the limb of a patient, to an inflated condition for at least partially sealing against the limb at the open end of the chamber. In addition, the method includes evacuating gas at least partially from at least one of the chamber and rib, and supplying a treatment gas to the chamber after the evacuating.

In still a further embodiment, a controller for controlling gas flow to and from a collapsible hyperbaric wound treatment device includes first, second and third control valves adapted for coupling to an inflatable sleeve, a treatment chamber and an inflatable rib, respectively, of the device. Within the device, the inflatable rib is for retaining the device in a rigid state, the treatment chamber includes an open end for receiving a limb of a patient and the inflatable sleeve is for sealing against the limb at the open end of the chamber when the sleeve is an inflated condition. The controller further includes a processor for selectively controlling the control valves and for selectively providing that at least one of the first, second and third control valves is in fluid communication with a gas source or a pump. The processor is operable for controlling the third valve for inflating the rib with a gas at least partially, before the limb is received in the chamber; for controlling the first valve for inflating the sleeve for at least partially sealing the sleeve against the limb at the open end of the chamber; for controlling the second valve for evacuating gas at least partially from the chamber based on operation of the pump and after the inflating of the sleeve for sealing the sleeve against the limb; and for controlling the second valve for supplying a treatment gas to the chamber from the gas source.

In another aspect of the invention, a hyperbaric wound treatment apparatus includes a chamber having an interior and an open end in communication therewith, and an inflatable limb sleeve configured for receiving a limb and coupled to the chamber. The sleeve can be positioned at least partially within the interior of the chamber adjacent the open end. The apparatus further includes a gas conveyance assembly, which is coupled to the sleeve and the interior of the chamber and is for creating a negative pressure, and a control device coupled to the gas conveyance assembly. The control device is operable for controlling the gas assembly for inflating the sleeve to an inflated condition for at least partially sealing against the limb adjacent the open end of the chamber, with the sleeve at least partially within the interior of the chamber at the open end; and for creating a negative pressure with the interior of the chamber by evacuating gas from the interior of the chamber, after the inflating of the sleeve.

In a further embodiment, a method of providing a treatment gas to a hyperbaric wound treatment device includes, after inserting a limb through an inflatable sleeve and into an interior of a chamber of the device, where the chamber has an open end in communication with the interior and the inflatable sleeve is coupled to the chamber and can be positioned at least partially within the interior of the chamber adjacent the open end, inflating the limb sleeve to an inflated condition for creating at least a partial seal between the limb and the sleeve adjacent the open end, with the sleeve at least partially within the interior of the chamber. The method also includes, after creating the seal, evacuating at least partially gas from within the interior of the chamber, and supplying a treatment gas to the interior of the chamber, following the evacuation of the gas from the interior of the chamber.

Additional features and advantages of the invention will become apparent to those skilled in the art upon consideration of the following detailed description of the disclosed embodiments.

BRIEF DESCRIPTION OF THE DRAWINGS

The various objects, advantages and features of this invention will be more fully apparent from a reading of the following detailed description in conjunction with the accompanying drawings in which like reference numerals refer to like parts, and in which.

DETAILED DESCRIPTION

Figure 1:
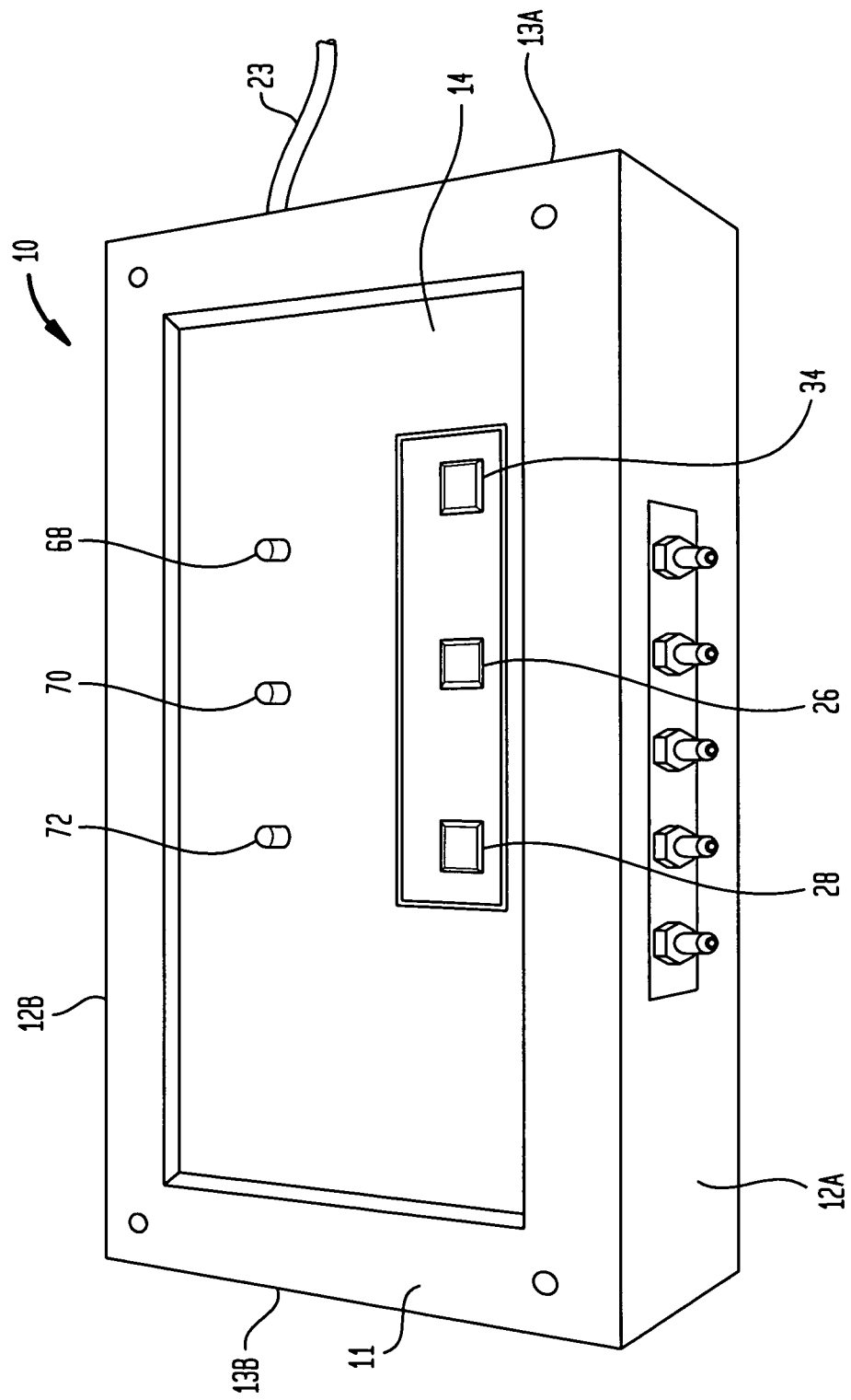
FIG. 1 is a perspective view of an exemplary controller in accordance with one aspect of the present invention.

FIG. 1 is a perspective view of a hyperbaric controller 10 adapted to control the operations of a flexible hyperbaric wound treatment device, in accordance with an aspect of the present invention. The controller 10 is desirably portable and can be easily picked up and moved to different operating locations by an operator. A housing 11 for the controller 10 includes side panels 12A, 12B, end panels 13A, 13B, a bottom panel (not shown) and a top panel 14. Although the embodiment of the invention discussed below and illustrated in the drawings is a flexible type wound treatment chamber, it is to be understood that the controller, in accordance with the present invention, also be may be utilized with a rigid type of wound treatment chamber, such as described in U.S. Pat. No. 5,060,644.

Referring to FIG. 1, the top panel 14 has indicators or pilot lights 68, 70, 72, which indicate operating modes or cycles such as "fill ribs," "fill cuff," and "hyperbaric therapy," respectively, and switches 26, 28, 34 which control the operation of the controller 10 and are labeled "cuff fill," "stop" and "start," respectively. Thus, the controller 10 includes switches that are easy to understand and easy to use, and indicators that alert the user as to the particular operation being performed. In an alternative embodiment, in addition to the pilot lights, the indicators of the controller 10 may be in any other form, such as audio, visual or both.

Figure 2:
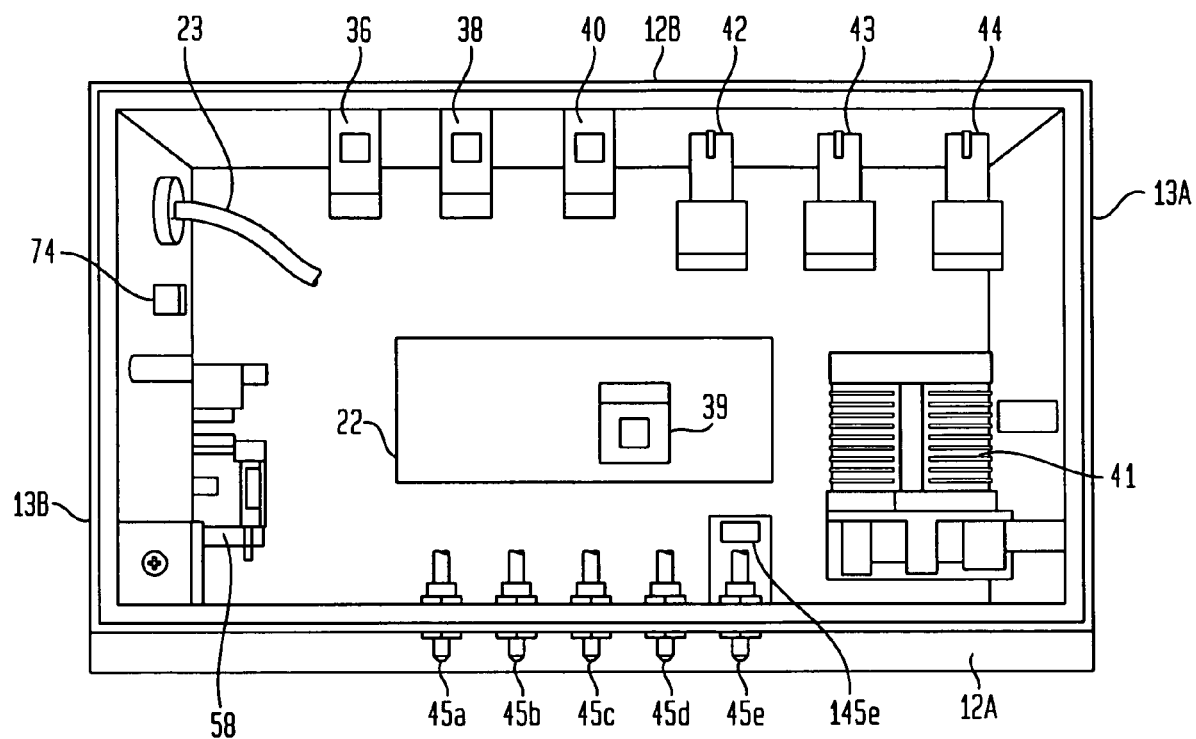
FIG. 2 is a view of the interior of the controller of FIG. 1.

Referring also to FIG. 2, air solenoid control valves 36, 38, 40 and pressure relief valves 42, 43, 44 are mounted to the rear side panel 12B of the housing 11. A vacuum pump 41 is mounted to the end panel 13A and a power supply 58, including a power switch 74 and a 120 VAC power supply cord 23, is mounted to the end panel 13B. The air solenoid control valves can be Clippard MME-3PDS (Clippard Instrument Laboratory, Cincinnati, Ohio), the pressure relief valves can be an Airtrol RV-5300-10-W/K (Airtrol Components Inc. New Berlin, Wis.) and the vacuum pump can be a Medo VP0125-V1005-D2-0511 (Medo USA, Hanover Park, Ill.). In addition to the air solenoid control valves, the controller 10 may incorporate any type of valve or the like to perform its operations, as known in the art. Further, in addition to the pressure relief valves, other types of valves may be utilized. In addition to the solenoids mentioned herein, proportional solenoids may also be utilized.

Figure 3:
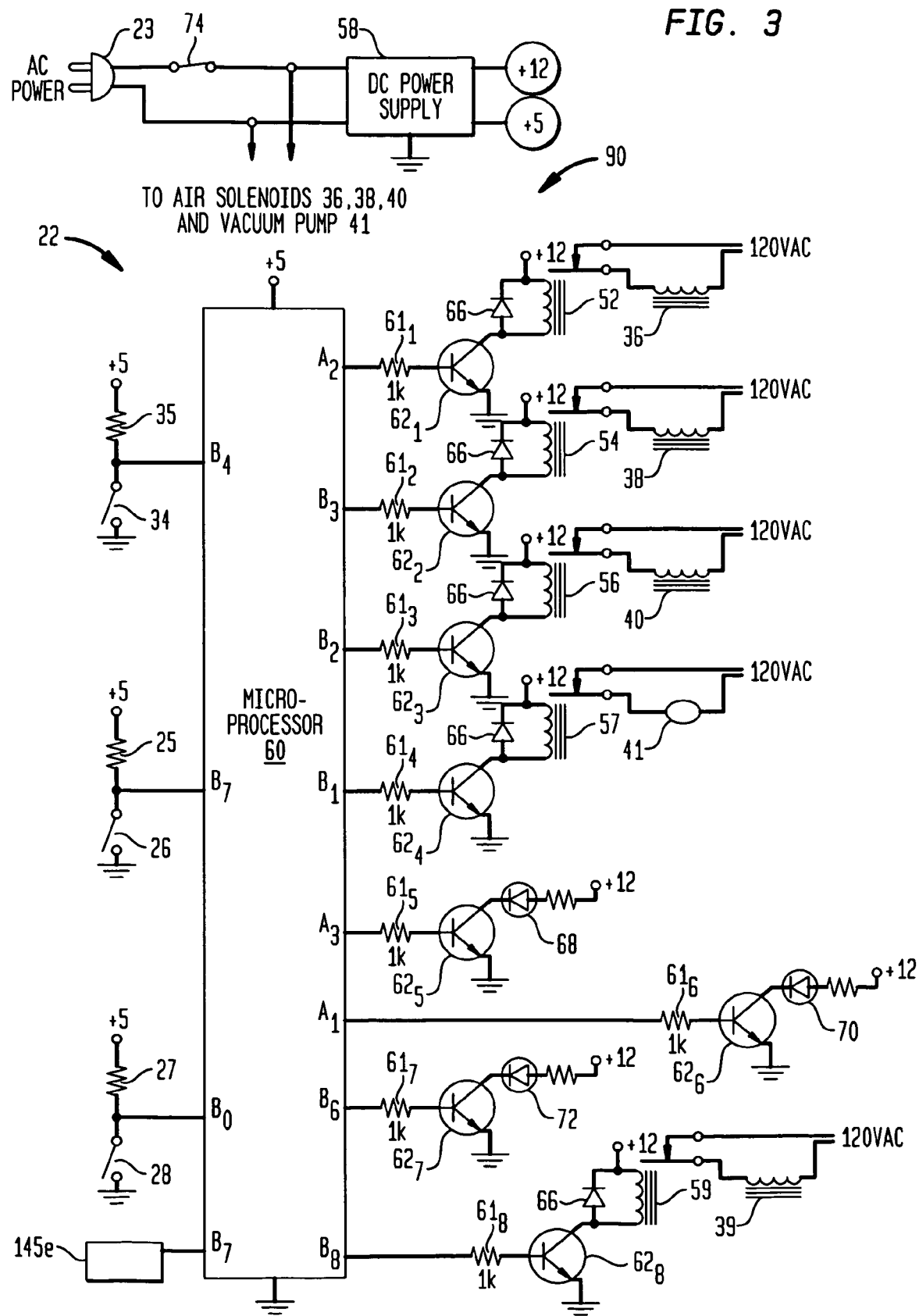
FIG. 3 is a partial schematic, block diagram of exemplary control circuits under control of a control module of a controller in accordance with an embodiment of the present invention.
Figure 5:
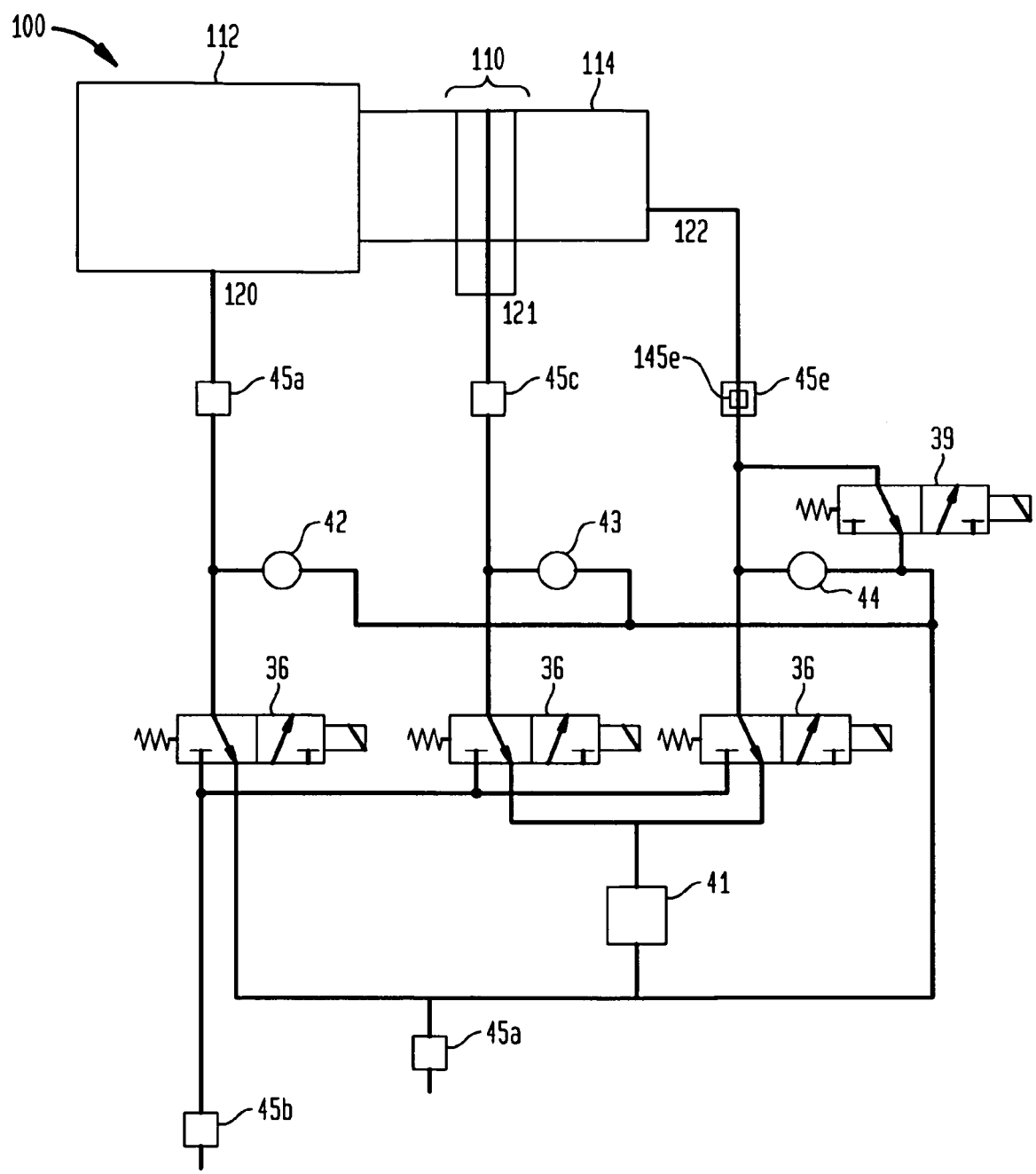
FIG. 5 is a partial schematic, block diagram of a controller coupled to a hyperbaric wound treatment device, in accordance with an aspect of the present invention.

Still referring to FIG. 2 and also referring to FIGS. 3 and 5, treatment gas, such as oxygen, from a supply source (not shown) is admitted into the controller 10 via a port 45b, which is mounted to the side panel 12A, and routed to the supply ports of the respective control valves 36, 38, 40. Input and output ports 45c, 45d, and input and output port assembly 45e, are mounted to the side panel 12A and connected to the control valves 38, 36 and 40, respectively. The assembly 45e includes a conventional pressure sensor 145e, which is electrically connected to a microprocessor 60 of the controller 10. Pressure relief valves 42, 43, 44 are connected to the flow paths, respectively, between the control valves 36, 38 and 40 and the ports 45*d*, 45*c* and the port assembly 45*e*. The vacuum pump 41 is connected to the exhaust ports of the air control valves 38, 40. The exhaust ports of the relief valves 42, 43, 44, the vacuum pump 41 and the cuff control valve 36 are routed to a vent port 45*a* mounted to the side panel 12A. Tubing to interconnect the ports and port assemblies, the control valves, the relief valves and the pump 41 can be conventional ¼" diameter tubing. Tubing for the exhaust lines connected to the vent port 45*a* can be conventional ⅛" diameter tubing. Any device or configuration may be utilized to control the flow of gas, including air and treatment gas, being introduced into or evacuated from a chamber, a cuff or a rib of a wound treatment device.

Referring to FIGS. 2 and 3, the power cord 23 is fed to a switch 74 and to the power supply module 58 to generate +12V and +5V for powering electronic control circuits 90 in the controller 10. Control module 22 is attached to the top panel 14 and includes a programmable microprocessor 60 which is coupled to the control circuits 90 of the controller 10. As discussed in detail below, the microprocessor 60 of the control module 22 is operable to control the control circuits 90, which are coupled to the valves 36, 38, 40, to provide that gas may be conveyed to and from a hyperbaric wound device, through the valves 36, 38, 40. In one embodiment, the control module 22 can include a portion or all of the electronic circuitry of the control circuits 90 that connects to the control valves of the controller 10, and the operation of the microprocessor, the valves and the control circuits in combination can provide for conveyance of gas to and from a hyperbaric wound device. Any type of power configuration or power source may be utilized. For instance, the power source may be a battery.

Still referring to FIG. 3 and further referring to FIG. 5, the control circuits 90 are used to control the operation of each of the control valves 36, 38, 40 which provide for flow of gas, such as oxygen, to a flexible hyperbaric device 100. The 120 VAC power is applied by the main power switch 74 to power the supply module 58, which provides +12 V and +5 V for operating the control circuits 90. The control module 22 operates the functions of the controller 10, such as time, sequence, pressure sequence and intermittent compression. Intermittent compression is determined and regulated by the control module 22, optionally based on the pressure detected in a chamber 114 of the device 100 by the pressure sensor 145*e*, in accordance to techniques well known in the art.

The programmable microprocessor 60 provides for software program control of the controller 10. Although described in greater detail below, the microprocessor 60 generally includes instructions for operating the hyperbaric device 100, including a cuff 112, a rib 110 and the chamber 114, when in use. In one embodiment, the microprocessor 60 includes instructions on cycling, and cycles the gas in the chamber 114 of the device 100, desirably based on a signal received at B7 representative of the pressure in the chamber 114 as detected by the pressure sensor 145*e*. The microprocessor 60 receives a start signal from the switch 34, which is activated when the operator starts to prepare a patient for hyperbaric therapy. The microprocessor 60 provides output signals at ports A2, B1, B2, B3 to control the base of each transistor $62_1$, $62_2$, $62_3$, $62_4$, respectively. In an alternative embodiment, cycling may be done according to information input by the operator. The operator sets and adjusts the time for the therapy as desired. For example, for deep vein thrombosis ("DVT"), no cycling is performed.

The output current from the output signal ports A2, B1, B2, B3 is current limited with resistors $61_1$, $61_2$, $61_3$, $61_4$, respectively. The value of each of the resistors $61_1$, $61_2$, $61_3$, $61_4$ is desirably 1K ohms. Each control relay 52, 54, 56, 57 has a flyback diode 66 to suppress voltage transients which could otherwise damage the microprocessor 60. In addition to controlling the relays 52, 54, 56, 57, the microprocessor 60 also controls the three pilot lights "fill ribs" 68, "fill cuff" 70 and "hyperbaric therapy" 72. Each of the pilot lights 68, 70, 72 indicates to an operator of the controller 10 an operational cycle in which the controller 10 is actually operating. The pilot lights 68, 70, 72 are switched by transistors $62_5$, $62_6$, $62_7$, respectively, in response to an "ON" and "OFF" signal from the microprocessor 60. The microprocessor 60 may be Model PIC 16F84A, 8 bit microcontroller, with 1K bytes of internal ROM memory storage, manufactured by Microchip Technology, Inc. of Chandler, Ariz. The switching transistors $62_1$-$62_7$ are commonly available 2N3904. The control relays may be Model G2R-1S-AS1-DC12 manufactured by Omron Electronics LLC of Schaumburg, Ill. The microprocessor 60 may be any type of computer, processor or an electronic component capable of performing instructions stored within it.

Figure 6:
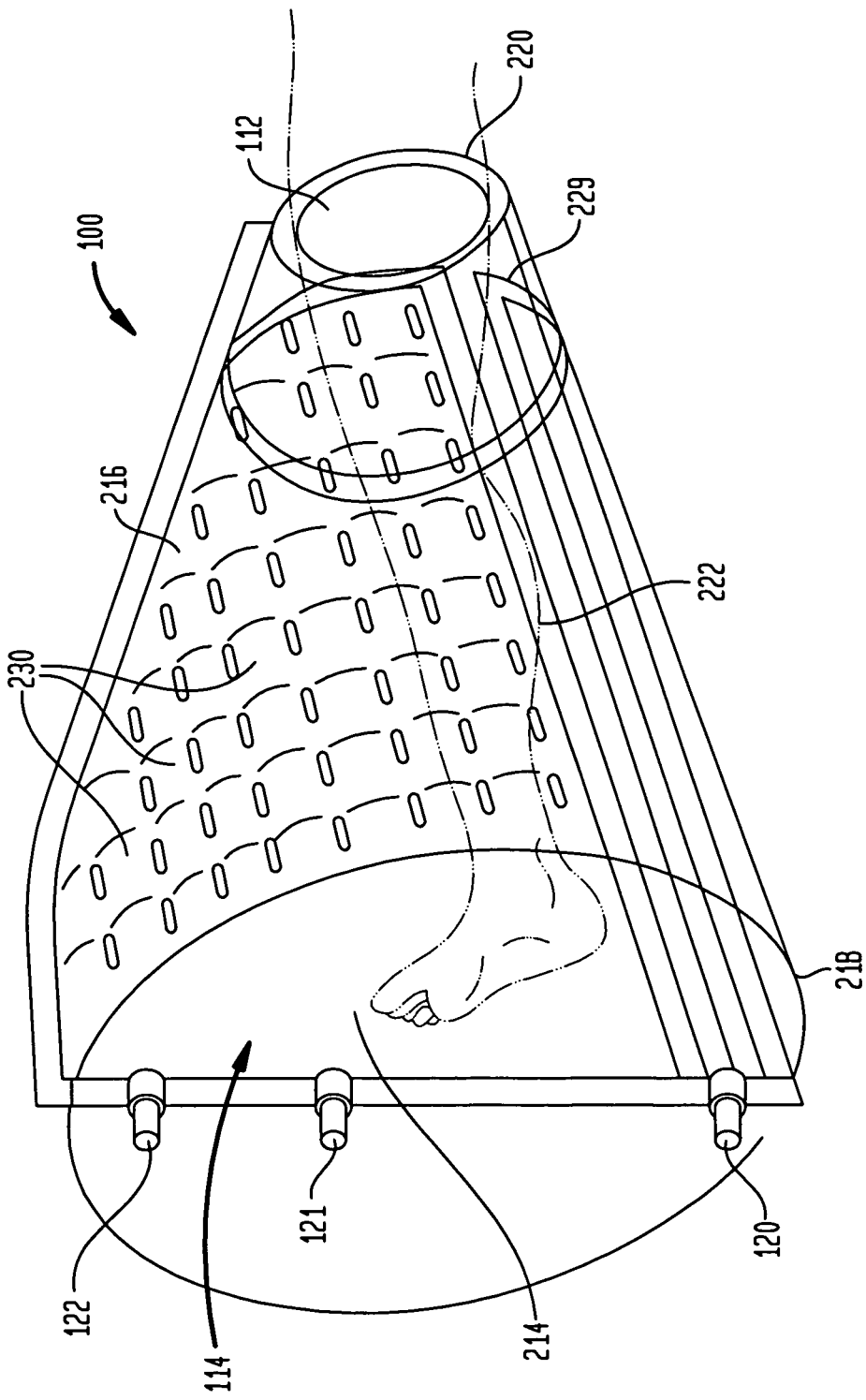
FIG. 6 is a schematic illustration of an embodiment of a hyperbaric wound treatment device.

FIG. 6 shows a topical hyperbaric wound treatment device 100, as disclosed in U.S. Patent Pub. No. 2006/0185670, the disclosure of which is incorporated by reference, having a main chamber 114 including an interior 214 and an exterior 216. The chamber 114 is closed at one end 218 and open at the other end 220, and sized and shaped to define the interior 214 for receiving a patient's limb, for example, a leg 222. Adjacent the other end 220 is an inflatable cuff seal 112 for sealing against the limb 222.

Figure 7:
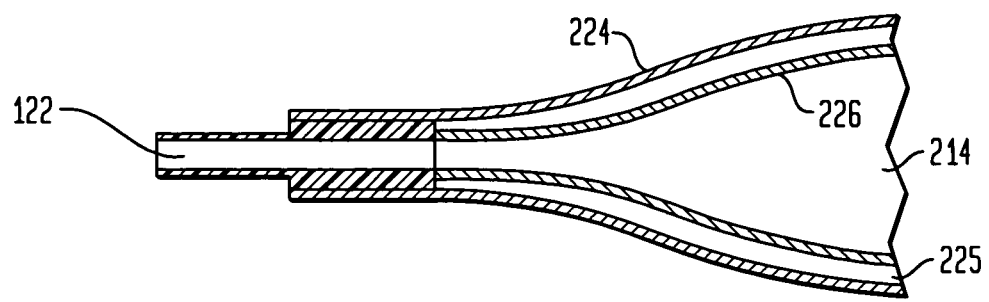
FIG. 7 is an illustration of an embodiment of a portion of the hyperbaric wound treatment device of FIG. 6.

Referring also to FIG. 7, the chamber 114 is defined by a collapsible bag including an outer sheet 224 and an inner sheet 226 defining a space 225 between the two sheets 224 and 226. The device 100 includes fluid ports 120, 121 and 122 which are in communication with the interior of the cuff 112, the space 225 and the interior 214 of the chamber 114, respectively, and through which gas can be conveyed based on operation of the controller 10. The ports 45*c*, 45*d* and port assembly 45*e* of the controller 10 are connected in fluid communication with the ports 121, 120, 122, respectively, of the device 100.

In one embodiment, gas can be delivered by the controller 10 to the space 225 between the sheets 224, 226 to inflate the device 100 to a rigid state and maintain the device 100 in the rigid state when gas pressure in the interior of the chamber 114 is cycled between about ambient pressure and above ambient pressure. In another embodiment, treatment gas inside the chamber 114 may be cycled by the controller 10 between at least about atmospheric or ambient pressure to a pressure of about up to 50 mm of mercury above atmospheric or ambient pressure.

Referring to FIG. 6, the device 100 may further include a plurality of interconnected pockets 230 or miniature chambers formed between the sheets 224, 226. The pockets can be formed by securing portions of the sheets of material together at selected, discrete locations. The sheets can be secured together at selected portions by any suitable means, such as by adhesively sealing the sheets together, heat sealing or ultrasonically welding the sheets together at selected, discrete points in an array resembling a waffle pattern. The present invention is not limited to a particular pattern for forming the interconnected pockets 230, and other patterns can be utilized.

Figure 8:
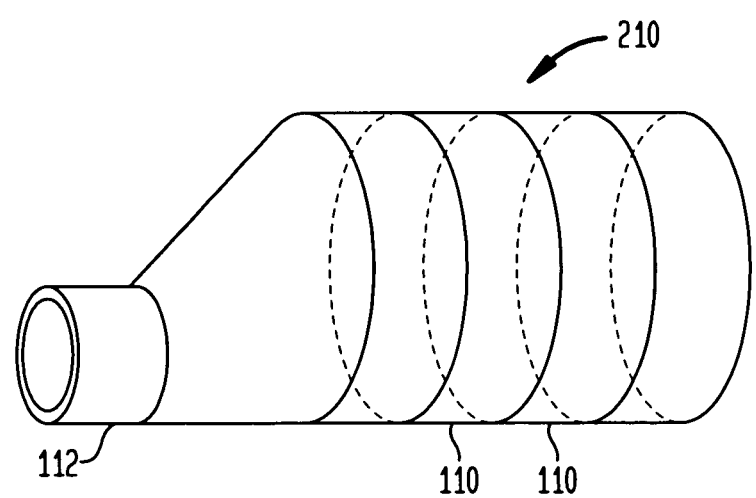
FIG. 8 is a schematic illustration of another embodiment of a hyperbaric wound treatment device.

FIG. 8 shows an additional embodiment of the present invention. Rather than utilize interconnected pockets 230, a hyperbaric treatment device 210 can have inflatable ribs 110 that extend at least partially along the sides of the device 210.

In this embodiment, the two sheets 224 and 226 may be affixed together in a linear fashion creating long passages or inflatable ribs 110 between the two sheets 224 and 226. The ribs 110 can encircle the chamber 114 entirely or partially, and there may be any number of such ribs 110. The ribs 110 may be formed in any of the manners listed previously.

Figure 4:
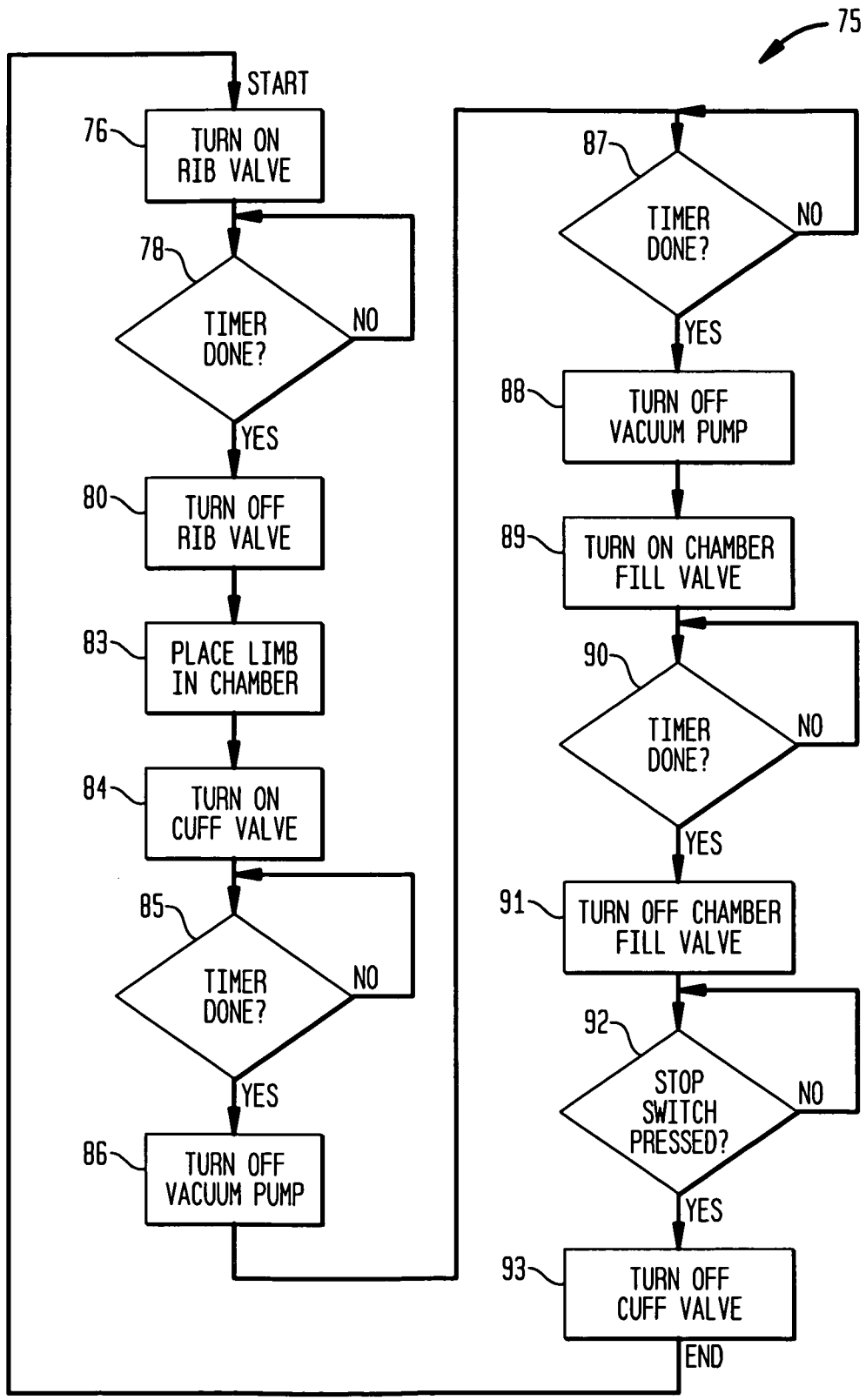
FIG. 4 is a flow chart of a process in accordance with an aspect of the present invention.

FIG. 4 is a flow chart 75 including operations that the microprocessor 60 may perform to control the operation of the controller 10. For purposes of illustrating the features of the invention, the operation of the controller 10 is described in connection with the hyperbaric device 100. Referring to FIG. 4, and also to FIGS. 1, 5 and 6, at block 76 an operator initiates a hyperbaric bag preparation cycle by turning on the main power switch 74, which initializes the microprocessor 60 and associated electronic control circuits 90. The operator presses the "start" switch 34, which sends a signal to the microprocessor 60. A signal is provided at the port B3 to turn-on the rib-fill valve 38, and also at the port A3 to turn-on the "fill ribs" pilot light 68. Oxygen, another gas, such as nitrogen, or ambient air, is supplied at the port 45c and inflates the ribs 110, with any excess oxygen flowing through the rib pressure relief valve 43 to the vent port 45a. In one embodiment, the valve 38 may control gas flow to and from the interconnected pockets 230 of the device 100

Next at block 78, the microprocessor 60 starts a timer for five minutes and checks to determine if the "stop" switch 28 is activated, which indicates that an operator wishes to arrest the preparation procedure. In the case where the "stop" switch 28 has been pressed, the microprocessor 60 commands the air solenoid control valves 36, 38 and 40 to the rest state, turns off the vacuum pump 41, if it is running, and extinguishes the pilot lights 68, 70 and 72, if they are illuminated. After the five minute timer has expired, in block 80 the microprocessor 60 commands the ports B3 and A3 to turn off the rib-fill air solenoid control valve 38 and extinguish the "fill ribs" pilot light 68, respectively.

With the ribs 110 now fully inflated, the patient's limb is placed in the chamber 114 at block 83 and the "cuff fill" switch 26 is activated. When the signal from the cuff fill switch is received by the microprocessor 60, the microprocessor 60 provides a signal at the port A2 to turn on the cuff-fill valve 36 and also provides a signal at the port A1 to turn on the "Fill Cuff" pilot light 70. It is to be understood that the cuff 112 may be inflated using air from the surrounding atmosphere, or other gas, such as nitrogen and the like.

Next, at block 85, the microprocessor 60 starts a timer for two minutes and checks to determine if the "stop" switch 28 is activated, which indicates that an operator wishes to arrest the preparation procedure. After the two minute timer has expired, the microprocessor 60 leaves both ports A1 and A2 switched on, which maintains oxygen flowing through the cuff-fill air solenoid control valve 36 and the valve 45d, and keeps the "Fill cuff" pilot light 70 illuminated. Excess oxygen flowing to the cuff 112 is vented by the pressure relief valve 42 and exits the controller 10 through the vent port 45a. With the cuff 112 now fully inflated, the flexible hyperbaric bag 100 is now sealed to the patient's limb.

Next, at block 86, the vacuum pump 41 is utilized to remove existing ambient air from the chamber 114. In some instances, the inflated ribs 110 can withstand this ambient air evacuation and stay rigid.

However, in other instances, depending on the size of the vacuum pump chosen, it may be advantageous to simultaneously evacuate the gas in both the chamber 114 as well as the ribs 110. This simultaneous evacuation can occur, because the evacuation of the chamber 114 places pressure on the chamber 114 walls and pulls them inwardly. Although the ribs 110 can remain inflated while the chamber 114 is evacuated, it has been found that this can place undue stress on the ribs 110. This stress results from the ribs 110 trying to stay rigid while the evacuation of the chamber 114 pulls the ribs 110 inwardly toward the wound. Therefore, to remove this undue stress on the ribs 110, evacuating the ribs 110 for a short period allows the ribs 110 to be pulled inwardly without the gas in the ribs 110 trying to counteract the pressure on the walls as the chamber 114 evacuation occurs. The ribs 110 and the chamber 114 can be evacuated in a manner such that the walls of the chamber 114 will not contact the wound. Thus, at block 86, the microprocessor 60 port B1 is commanded to +5 V, which in turn saturates the junction of transistor $62_4$ which engages the relay 57 causing the vacuum pump 41 to start removing gas from the ribs 110 and also gas from the therapy chamber 114. The gas may be evacuated up to about 95% of the gas initially within the chamber 114 prior to the commencement of the evacuation, such that about 5% of the gas, such as ambient air, initially within the chamber 114 remains within the chamber 114 following evacuation.

Alternatively, additional gas may be supplied to the ribs 110 to overcome the pressures within the chamber 114 during evacuation.

Next, at block 87, the microprocessor 60 starts a timer for five minutes and checks to determine if the "stop" switch 28 is activated, which indicates that an operator wishes to arrest the preparation procedure. At block 88, after the five-minute timer has expired, the microprocessor 60 commands the port B1 to turn off the vacuum pump 41. Now that the ribs 110 have been deflated and the chamber 114 has been evacuated, at block 89, the microprocessor 60 commands the port B2 to activate therapy chamber air solenoid control valve 40, and the port B3 to activate the valve 38. Treatment gas, such as oxygen, flows from the port 45b, through the valve 40 and the port assembly 45e and into the therapy chamber 114. In one embodiment, the ribs 110 are simultaneously inflated with air or gas when the treatment gas is supplied to the chamber 114. However, in the event that the ribs 110 had not been deflated, in block 89, only the chamber 114 is filled with oxygen and the treatment begins.

Next, at block 90, the microprocessor 60 starts a timer for five minutes and checks to determine if the "stop" switch 28 is activated. If during this block or at any time during the hyperbaric therapy session, the pressure in therapy chamber 114 exceeds 50 mm Hg above one atmosphere of pressure ("ATA") or 810 mm Hg, oxygen is vented by the pressure relief valve 44 and exits the control box 10 through the vent port 45a.

At block 91, after the five minute timer has expired, the microprocessor 60 commands the ports B2 and A1 to turn off the air solenoid control valve 40 and extinguish the "Fill Cuff" pilot light 70, respectively. The microprocessor 60 also commands port B6 on to illuminate "Hyperbaric Therapy" pilot light 72. Then the microprocessor 60 continues to determine if the "stop" button 28 has been pressed in block 92. Finally, at block 93, if the "stop" button 28 has been depressed because of either an emergency situation or the hyperbaric therapy treatment is completed, the microprocessor 60 commands ports A2 and B6 to shut off the oxygen flow to the cuff 112 and extinguish "hyperbaric therapy" pilot light 72. The oxygen in the cuff 112 now vents to the atmosphere via the exhaust port of air solenoid control valve 36, leaving controller 10 through the vent port 45a. Although timers can be used throughout, in an embodiment of the present invention, a timer may not be required or utilized for some or all of the blocks described herein. In the event a timer is not incorporated, depressing the stop button may simply halt the process currently underway. In another embodiment, instead of timers, event driven sensors, such as pressure sensors, or the like may be used.

The objects and illustrative embodiments of the hyperbaric therapy are fully disclosed in U.S. Pat. Pub. No. 2006/0185670A1 entitled "Hyperbaric oxygen devices and delivery methods," the disclosure of which is incorporated herein by reference.

In one embodiment, the controller 10 may also have a built-in safety feature should the pressure in the chamber 114 during treatment exceed its preset pressure, for example, a maximum pressure of 100 mm Hg above ATA, or 860 mm Hg. In such embodiment, referring to FIGS. 3 and 5, the controller 10 includes a port B8 connected through a 1K resistor $61_8$ to a base of a transistor $62_8$, and a control relay 59 with a flyback diode 66 couples the collector of the transistor $62_8$ to a dump (exhaust) air solenoid control valve 39. The controller 10 commands the port B8 to open the valve 39, which is in fluid communication with the port assembly 45e, when the "Stop" switch 28 is activated, to cause the chamber 114 to automatically decompress to 0 mm Hg and avoid the risk of a tourniquet effect. The tourniquet effect may be caused by the therapy pressure being set above capillary closure in the human body (16-33 mm Hg), or if a malfunction occurs, such that the pressure sensor does not operate correctly or the chamber 114 stays at a constant pressure above about 22 mm Hg. This safety feature of the controller 10 offers benefits to patients who suffer from chronic wounds, have very fragile vascular systems in their lower extremities and are at high risk of capillary closure. In an alternative embodiment, the controller 10 commands the port B8 to open the valve 39, based on a signal provided by the pressure sensor 145e, which is representative of the pressure within the chamber 114.

Figure 9:
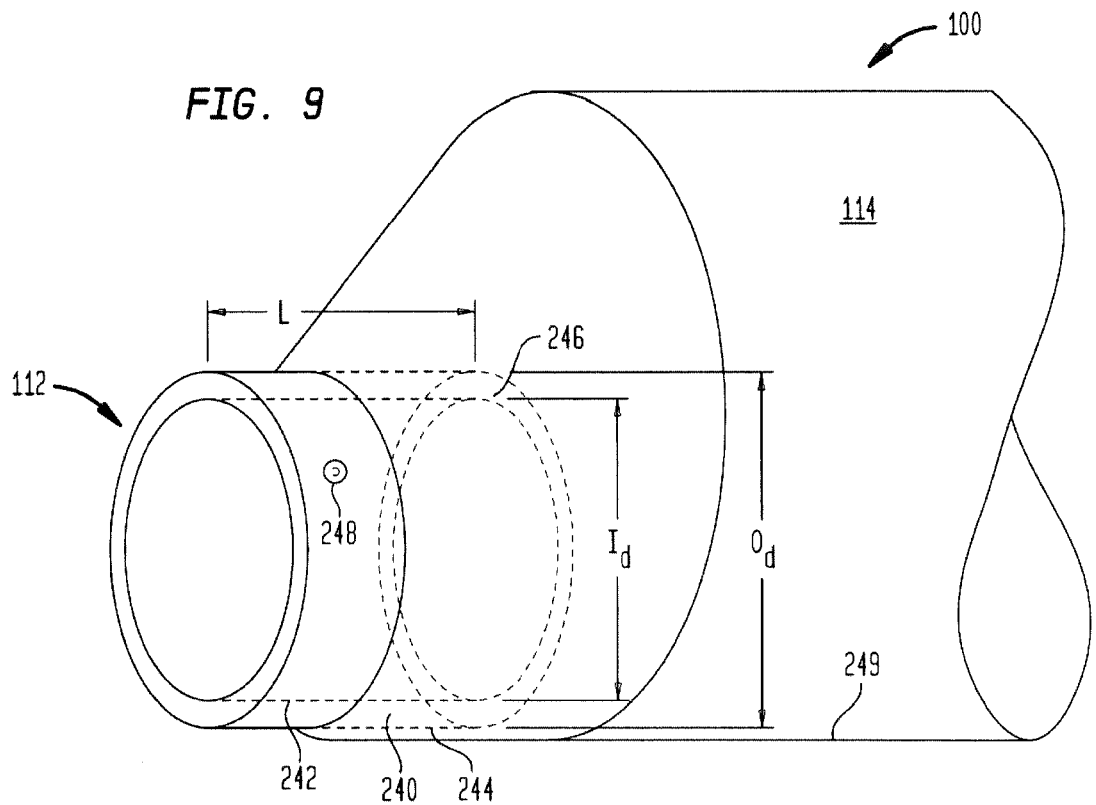
FIG. 9 is a schematic illustration of an embodiment of a seal for a hyperbaric wound treatment device.

In another aspect of the present invention as shown in FIG. 9, the cuff 112 of the hyperbaric treatment device 100 can be positioned partially or wholly inside the chamber 114 when in an inflated condition. Referring to FIG. 9, the cuff 112 includes a tubular inflatable sleeve 240 that can provide a hermetic seal against the limb when the limb is inserted through the sleeve 240 and into the chamber 114. The sleeve has a length L as well as an inside diameter Id and an outside diameter Od. The sleeve 240 further includes an inside wall 242, an outside wall 244 and a side wall 246 that connects the inside and outside walls, 242, 244. The inside diameter Id is formed from the inside wall 242, and the outside diameter Od is formed from the outside wall 244.

The sleeve 240 is inflated using an air valve 248 disposed on the sleeve 240. In one embodiment, the valve 248 is coupled in fluid communication with the valve 45d of the controller 10. Air or any suitable gas is introduced between the inside and outside walls, 242, 244 to inflate the sleeve 240. Prior to inflation, the inside diameter Id is X. Upon inflation, the inside diameter is less than X. This ensures that the sleeve 240 diameter, prior to inflation, is large enough to accommodate a limb sliding through the sleeve 240, but the diameter can be decreased enough to snugly encircle another portion of the limb that is not for treatment. In one embodiment, the sleeve 240 is configured to have a sufficiently large diameter in a non-inflated or partially inflated condition, such that a portion of a limb to be inserted into the chamber 114 for treatment can be slid through the sleeve 240, when the sleeve 240 is in such condition, without the portion of the limb contacting the sleeve inside wall 242, while providing that the diameter also can be decreased enough to snugly encircle another portion of the limb that is not for treatment.

In one embodiment, the outside wall 244 and the side wall 246 may have a thickness greater than the thickness of the inside wall 242. This difference in thickness ensures that when the sleeve 240 is inflated, the thicker walls generally resist flexure and maintain their size and dimension, allowing the inside wall 242 to absorb the inflation. Thus, due to its smaller thickness, the inside wall 242 will stretch and accommodate the inflation, allowing the inside diameter Id to decrease to a size sufficient to seal against a limb. This also allows the sleeve 240 to seal well against any variations in the limb size or shape, such as a knee or ankle.

In one embodiment, the sleeve wall thicknesses are larger than the thickness of the chamber walls, formed by the sheets 224 and 226. This is because the sleeve 240 must withstand the pressures within the sleeve due to inflation of the sleeve 240 and pressure on the outside of the sleeve from the gas in the chamber 114. Thus, the sleeve 240 is acted on by pressures from inside the sleeve 240 and inside the chamber 114. The pressure within the sleeve 240 is much smaller than the maximum pressure in the chamber 114. Therefore, the pressures internal and external to the sleeve 240 do not cancel out.

An advantage of placing the sleeve 240 within the chamber 114 is to ensure that the incidence of the sleeve 240 sliding off the limb is reduced. The gas inside the chamber 114 places positive pressure on the outside wall 244 and retains the sleeve 240 in place on the limb. During inflation, the sleeve 240 can be inflated up to 1 psi of pressure. Thus, less pressure is required to maintain the sleeve 240 on the limb than with other types of wound treatment seals or sleeves placed on the outside of the chamber 114.

This type of sleeve 240, placed inside the chamber 114, can be incorporated with reusable chambers, chambers having rigid structures such as disclosed in U.S. Pat. No. 5,060,644 which is hereby incorporated by reference, as well as single use chambers where these sleeves 240 can replace the latex seals that are now used. This is especially advantageous in that some patients have an adverse reaction to latex.

Still referring to FIG. 9, in an alternative embodiment of the device 100, the outside wall 244 of the sleeve 240 is attached to an interior wall surface 249 of the chamber 114. In addition, the sleeve 240 is made of sufficiently flexible material, such that the sleeve 240 can be folded or rolled into itself, when the sleeve 240 is not inflated or minimally inflated. In one desired embodiment, the sleeve 240 can be folded so that the sleeve 240 is not within the interior 114 of the device 100 when the interior 114 is not inflated or minimally inflated.

References to the hyperbaric chamber device 100 are exemplary only and it should be noted that the controller 10 described herein can be used with any type of hyperbaric chamber. For example, the controller 10 can be used with reusable chambers, a topical hyperbaric chamber such as a torso or abdominal chamber or a single use hyperbaric chamber having several internal rings that form a plurality of chambers within the chamber 114. The controller can also be configured for use with chambers that treat wounds by means of evacuation or chambers that perform compression therapy or a combination of a variety of treatments.

Figure 10:
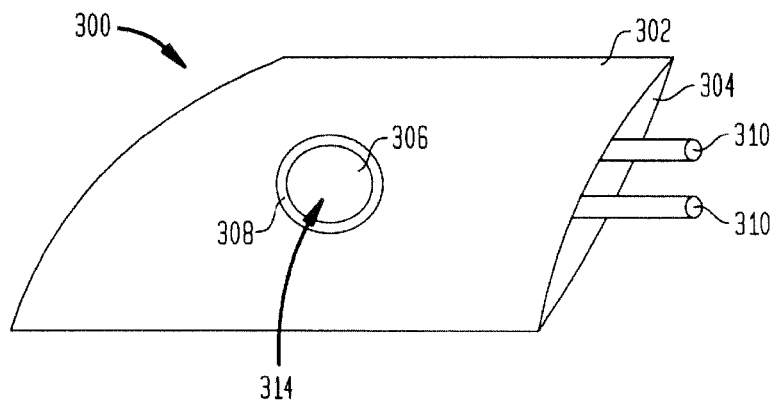
FIG. 10 is a schematic illustration of a topical hyperbaric wound treatment device for use with a controller in accordance with the present invention.

In an embodiment of the present invention, the controller 10 described herein can be utilized with a topical hyperbaric chamber device 300, as illustrated in FIG. 10. See U.S. Pat. No. 5,154,697, which is also incorporated by reference herein. Referring to FIG. 10, the topical device 300 includes a top sheet 302 and a bottom sheet 304 defining an interior region 314. In addition, the topical chamber 300 includes an opening 306 having a seal 308 for affixing to a patient and in communication with the region 314. Further, the topical chamber 300 includes couplers 310 that connect to the vacuum pump 41 and a valve of the controller 10. Once affixed to a patient, the topical chamber 300 can be operated by the controller 10 in a manner similar to that of the device 100.

Although the invention herein has been described with reference to particular embodiments, it is to be understood that these embodiments are merely illustrative of the principles and application of the present invention. It is therefore to be understood that numerous modifications may be made to the illustrative embodiments and that other arrangements may be devised without departing from the spirit and scope of the present invention as defined by the appended claims.

The invention claimed is:

1. A hyperbaric wound treatment device comprising:
    a chamber having an interior and an open end in communication therewith; and
    an inflatable tubular limb sleeve configured for sealing against the limb of a patient including an inner wall spaced apart from an outer wall forming an interior region therebetween for receiving an inflation gas, the inner wall and the outer wall coupled to the open end of the chamber and extending away therefrom, the inner wall and the outer wall of the sleeve configured to be positioned between a first orientation and a second orientation, wherein the first orientation comprises the inner wall and the outer wall of the sleeve extending from the open end of the chamber wholly outwardly of the interior of the chamber, wherein the second orientation comprises the inner wall and the outer wall of the sleeve extending from the open end of the chamber wholly within the interior of the chamber, and wherein the inner wall and the outer wall of the sleeve is positionable between the first and second orientations at least partially within the interior of the chamber and partially outside the interior of the chamber adjacent the open end of the chamber.

2. The device of claim 1, wherein the limb sleeve is configured for receiving a limb, and for sealing against the limb adjacent the open end of the chamber when the sleeve is in an inflated condition.

3. The device of claim 1, wherein the limb sleeve is configured for receiving a limb and includes the outer wall defining an outer diameter and the inner wall defining an inner diameter, and wherein, in an inflated condition with a limb received in the sleeve, the inner wall is in sealing contact with the limb and the outer wall defines a portion of the interior of the chamber.

4. The device of claim 3, wherein the outer wall has a thickness greater than a thickness of the inner wall.

5. The device of claim 3, wherein, in the inflated condition of the sleeve, the inner diameter of the inner wall is less than its inner diameter prior to inflation of the sleeve to the inflated condition, and the outer diameter of the outer wall is substantially the same as its outer diameter prior to inflation of the sleeve to the inflated condition.

6. The device of claim 3, wherein, when the limb is received in the sleeve and the sleeve is in the inflated condition, a pressure within the sleeve is less than a pressure in the interior of the chamber.

7. The device of claim 1, wherein the sleeve includes a valve through which a gas is conveyable into and out of the interior region of the sleeve.

8. The device of claim 1, wherein the chamber comprises a collapsible bag having an opening at the open end of the chamber and sized and shaped to receive a limb and wherein, in an inflated condition of the sleeve with a limb received in the bag, the sleeve is positioned at least partially within the bag for sealing against the limb.

9. The device of claim 1, wherein the inner wall is substantially more deformable than the outer wall.

10. A hyperbaric wound treatment apparatus comprising:
    a chamber having an interior and an open end in communication therewith;
    an inflatable tubular limb sleeve configured for sealing against the limb of a patient including an inner wall spaced apart from an outer wall forming an interior region therebetween for receiving an inflation gas, the inner wall and the outer wall coupled to the open end of the chamber and extending away therefrom, the inner wall and the outer wall of the sleeve configured to be positioned between a first orientation and a second orientation, wherein the first orientation comprises the inner wall and the outer wall of the sleeve extending from the open end of the chamber wholly outwardly of the interior of the chamber, wherein the second orientation comprises the inner wall and the outer wall of the sleeve extending from the open end of the chamber wholly within the interior of the chamber, and wherein the inner wall and the outer wall of the sleeve is positionable between the first and second orientations at least partially within the interior of the chamber and partially outside the interior of the chamber adjacent the open end of the chamber;
    a gas conveyance assembly coupled to the sleeve and the interior of the chamber and for creating a negative pressure; and
    a control device coupled to the gas conveyance assembly operable for controlling the gas assembly for:
        inflating the sleeve to an inflated condition for at least partially sealing against the limb adjacent the open end of the chamber, with the sleeve at least partially within the interior of the chamber between the first and second orientations at the open end; and
        creating a negative pressure within the interior of the chamber by evacuating gas from the interior of the chamber, after the inflating of the sleeve.

11. The apparatus of claim 10, wherein the gas conveyance assembly is operable for supplying a treatment gas to the interior of the chamber from a treatment gas supply, following the evacuating of the interior of the chamber.

12. The apparatus of claim 11, wherein the treatment gas is supplied to the interior of the chamber to maintain the interior of the chamber at a pressure exceeding the pressure within the sleeve in the inflated condition.

13. The apparatus of claim 12, wherein the pressure maintained in the interior of the chamber exceeds the pressure within the sleeve in the inflated condition, such that the pressure in the interior of the chamber contributes to the sealing of the sleeve against the limb.

14. The apparatus of claim 10, wherein the sleeve includes the outer wall defining an outer diameter and the inner wall defining an inner diameter, and wherein, in the inflated condition with the limb received in the sleeve, the inner wall is in sealing contact with the limb and the outer wall defines a portion of the interior of the chamber.

15. The apparatus of claim 14, wherein the outer wall has a thickness greater than a thickness of the inner wall.

16. The apparatus of claim 14, wherein, in the inflated condition of the sleeve, the inner diameter of the inner wall is less than the inner diameter of the inner wall prior to inflation of the sleeve to the inflated condition and the outer diameter of the outer wall is substantially the same as the outer diameter of the outer wall prior to inflation of the sleeve to the inflated condition.

17. The apparatus of claim 10, wherein, when the sleeve is in the inflated condition, a pressure within the sleeve is less than a pressure in the interior of the chamber.

18. The apparatus of claim 10, wherein the gas conveyance assembly includes a valve means through which a gas is conveyable into and out of the interior region of the sleeve and the chamber, respectively.

19. The apparatus of claim 10, wherein the chamber comprises a collapsible bag having an opening at the open end of the chamber and sized and shaped to receive the limb and an inflatable rib for retaining the bag in a rigid state, wherein the control device is operable to control the gas conveyance assembly for:

inflating the rib at least partially before the inflating of the sleeve to the inflated condition.

20. The apparatus of claim 18, wherein the control device is operable to control the gas conveyance assembly for:

supplying a gas to the rib under pressure during or after the evacuation of gas from the interior of the chamber.

21. The apparatus of claim 10, wherein the gas conveyance assembly includes at least one of a pump and a control valve.

22. The apparatus of claim 10, wherein the control device is operable to control the gas conveyance assembly for:

supplying a gas from a gas source under pressure to the chamber, after the evacuating of the gas at least partially from the interior of the chamber.

23. The device of claim 1, wherein the inner wall and the outer wall of the sleeve is folded upon itself when the sleeve is arranged between the first and second orientations.

24. The device of claim 23, wherein the outer wall forms a seal in contact with the patient's limb when the sleeve is in the second orientation.

25. The device of claim 1, wherein the inner wall forms a seal in contact with the patient's limb when the sleeve is in the first orientation.

26. The apparatus of claim 10, wherein the inner wall and the outer wall of the sleeve is folded upon itself when the sleeve is arranged between the first and second orientations.

27. The apparatus of claim 26, wherein the outer wall forms a seal in contact with the patient's limb when the sleeve is in the second orientation.

28. The apparatus of claim 10, wherein the inner wall forms a seal in contact with the patient's limb when the sleeve is in the first orientation.

* * * * *

UNITED STATES PATENT AND TRADEMARK OFFICE
CERTIFICATE OF CORRECTION

PATENT NO. : 8,529,527 B2  
APPLICATION NO. : 12/156466  
DATED : September 10, 2013  
INVENTOR(S) : Phillip Loori et al.

Page 1 of 1

It is certified that error appears in the above-identified patent and that said Letters Patent is hereby corrected as shown below:

In the Claims

Column 11, line 31, "is" should read -- are --.  
Column 12, line 22, "is" should read -- are --.  
Column 14, line 6, "is" should read -- are --.  
Column 14, line 5, "itself" should read -- themselves --.  
Column 14, line 14, "is" should read -- are --.  
Column 14, line 14, "itself" should read -- themselves --.

Signed and Sealed this  
Fourth Day of August, 2015

Michelle K. Lee  
*Director of the United States Patent and Trademark Office*